United States Patent [19]

Heyn

[11] Patent Number: 5,610,713
[45] Date of Patent: Mar. 11, 1997

[54] DEVICE FOR MEASURING THE OPTICAL RANGE OF OPTICAL AND ELECTRONICS SYSTEMS

[75] Inventor: Klaus Heyn, Hamburg, Germany

[73] Assignee: Jenoptik AG, Jena, Germany

[21] Appl. No.: 483,445

[22] Filed: Jun. 7, 1995

[30] Foreign Application Priority Data

May 31, 1995 [EP] European Pat. Off. ............. 95108334

[51] Int. Cl.$^6$ .................................................. G01N 21/47
[52] U.S. Cl. ......................... 356/342; 250/574; 250/575; 356/437
[58] Field of Search ................................. 356/342, 435, 356/438, 439, 437; 250/573–575

[56] References Cited

U.S. PATENT DOCUMENTS 3,872,315  3/1975  Boll .......................................... 356/439

*Primary Examiner*—F. L. Evans
*Attorney, Agent, or Firm*—Cohen, Pontani, Lieberman & Pavane

[57] ABSTRACT

The present invention is directed to an optical range measurement device which is able to compensate for lens contamination. The optical range measurement device includes one or more windows having at least two sections positioned at an angle to one another, a transmitter for producing a main beam and transmitting the main beam into the atmosphere, and a receiver for receiving the main beam back scattered by the atmosphere. The device also includes a transmitter producing a reference beam which illuminates the at least two sections and a receiver for receiving the reference beam.

4 Claims, 4 Drawing Sheets

DEVICE FOR MEASURING THE OPTICAL RANGE OF OPTICAL AND ELECTRONICS SYSTEMS

BACKGROUND OF THE INVENTION

1. Field of the Invention

The present invention relates to optical range measurement devices having transmitters and receivers as well as to the necessary optical devices and analysis devices.

2. Description of the Related Art

In optical range measurement devices of this type, windows are basically used to protect the optical and electronic systems. The contamination of these windows is a constant problem. At airports, in particular, it must be possible to ascertain optical ranges, despite the especially heavy contamination resulting from aircraft exhaust.

SUMMARY OF THE INVENTION

It is accordingly an object of the present invention ascertain optical ranges of optical and electronics systems despite contamination of windows protecting the systems. Into an optical range measurement device having one or more windows and at least one main beam path which radiates through and illuminates the atmosphere, the invention calls for windows to be arranged in such a way that these windows always have at least two sections positioned at an angle to one another or capable of being positioned at an angle and for these sections to be illuminated by an extra transmitter and receiver beam path. In terms of its function, this extra beam path serves as a reference beam path for ascertaining lens contamination. The reference beam path does not serve to radiate through the atmosphere. The term "extra beam path" is used here only to explain this path and delineate it from the main beam path. The term does not mean that a main beam path for radiating through the atmosphere and a reference beam path for ascertaining lens contamination must necessarily be radiated at the same time. Rather, turning the transmitting and receiving device for the main beam path permits the main beam path to be used as the reference beam path for ascertaining lens contamination. It is also possible, instead of turning the main beam path, to turn the lenses in the main beam path. It matters only that radiation of a beam through the atmosphere and radiation of a reference beam for ascertaining lens contamination are carried out simultaneously or in chronological sequence.

DETAILED DESCRIPTION OF THE PRESENTLY PREFERRED EMBODIMENTS

Figure 1:
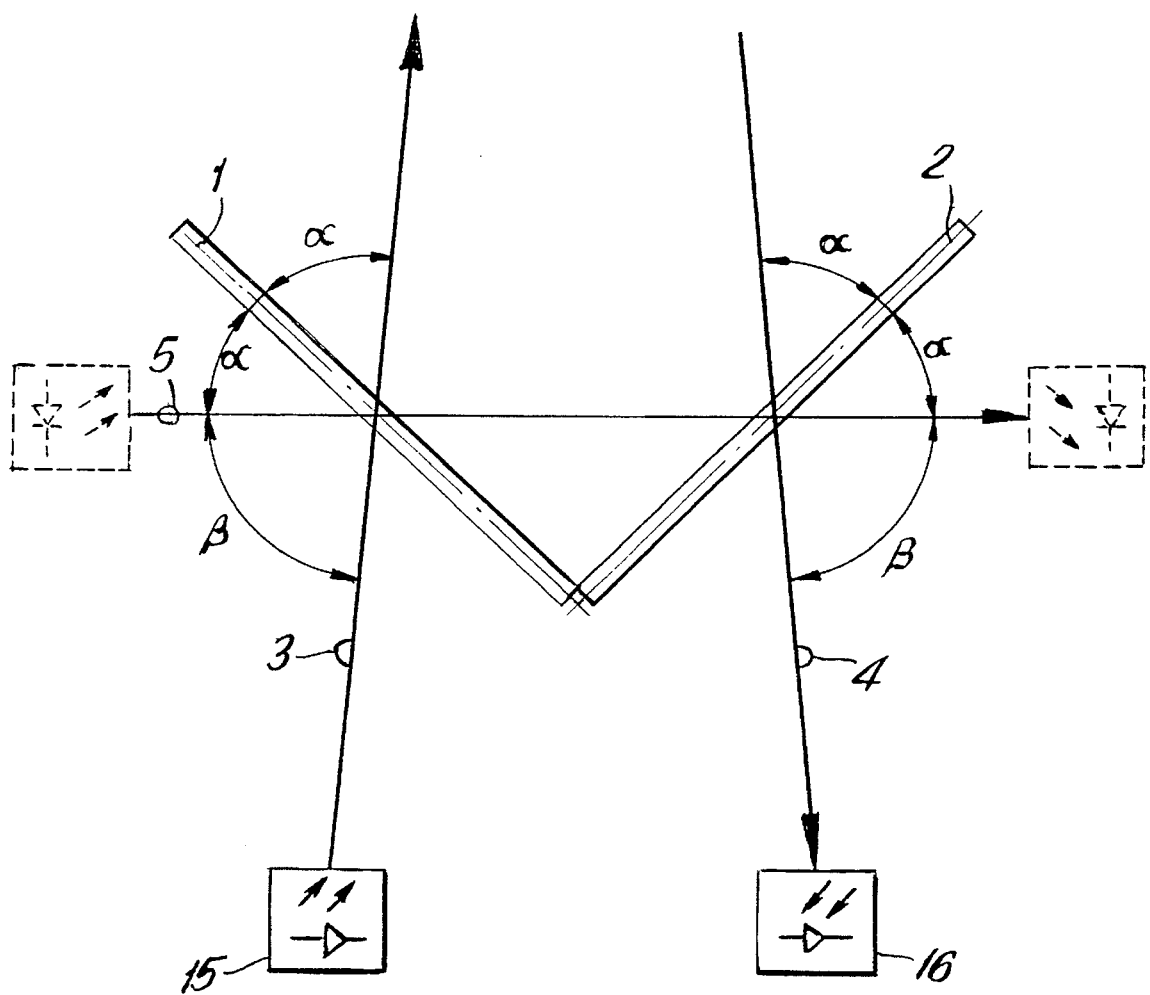
FIG. 1 is a schematic view of a window of the present invention having a main and reference beam radiating therethrough.

The present invention will now be described with reference to FIGS. 1–4. In FIG. 1, the window consists of the angled sections or lenses 1, 2. The main beam 3 comes from a transmitter 15 and radiates through the atmosphere. In this example, a received beam 4 back-scattered by the atmosphere is received by a receiver 16. Through movement of the transmitter producing for the main beam 3 and the received beam 4, the main beam becomes the reference beam 5. This movement of the transmitter 15 and the receiver 16 is shown in dashed lines in FIG. 1. With respect to the angle between the angled sections or lenses 1 and 2 of the window, it matters only that radiation be permitted in the direction of the reference beam 5. Depending on the given geometry, e.g., the size of the transmitter and the receiver, an appropriate angle is set between the sections or lenses 1 and 2. Preferably, the sections or lenses 1 and 2 are arranged relative to the main beam 3 and received beam 4 in such a way that the angle α between lens 1 and main beam 3 corresponds to the angle α between lens 2 and received beam 4. This ensures that the deposits on both windows are illuminated at the same angle, for the transmitted beam as well as the received beam 4. Furthermore, it is preferable for the angle between lens 1 and reference beam 5 to be exactly as large as the angle α between lens 1 and main beam 3. The same applies to section or lens 2. Furthermore, it is preferable for the reference beam 5 to illuminate substantially the same area on the angled sections or lens 1 and 2 as the main beam path 3, 4.

According to a preferred embodiment as shown in FIG. 1, a reference beam path 5 is arranged next to the main beam path 3, 4. In this case, the angled sections of the window are oriented to bisect the angle formed between the main beam 3, 4 and the reference beam 5. This is illustrated in FIG. 1 by the angles labeled α and β whereby, as is well known and easily determined using basic geometry, it is illustrated that β+2α=180°. The reference beam 5 thus has its own transmitter and its own receiver.

Figure 3:
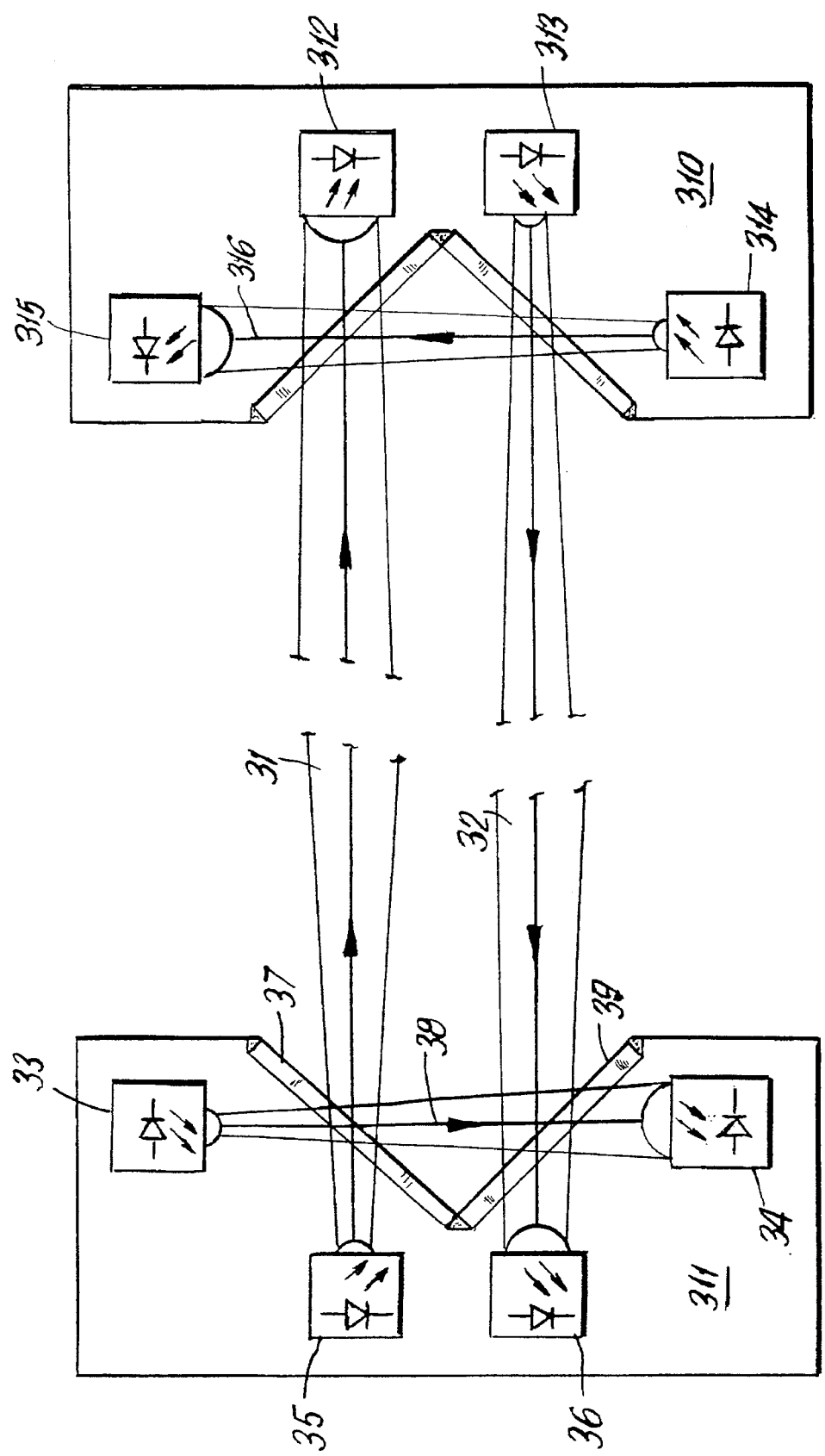
FIG. 3 is a schematic side view of a third embodiment of the present invention.
Figure 4:
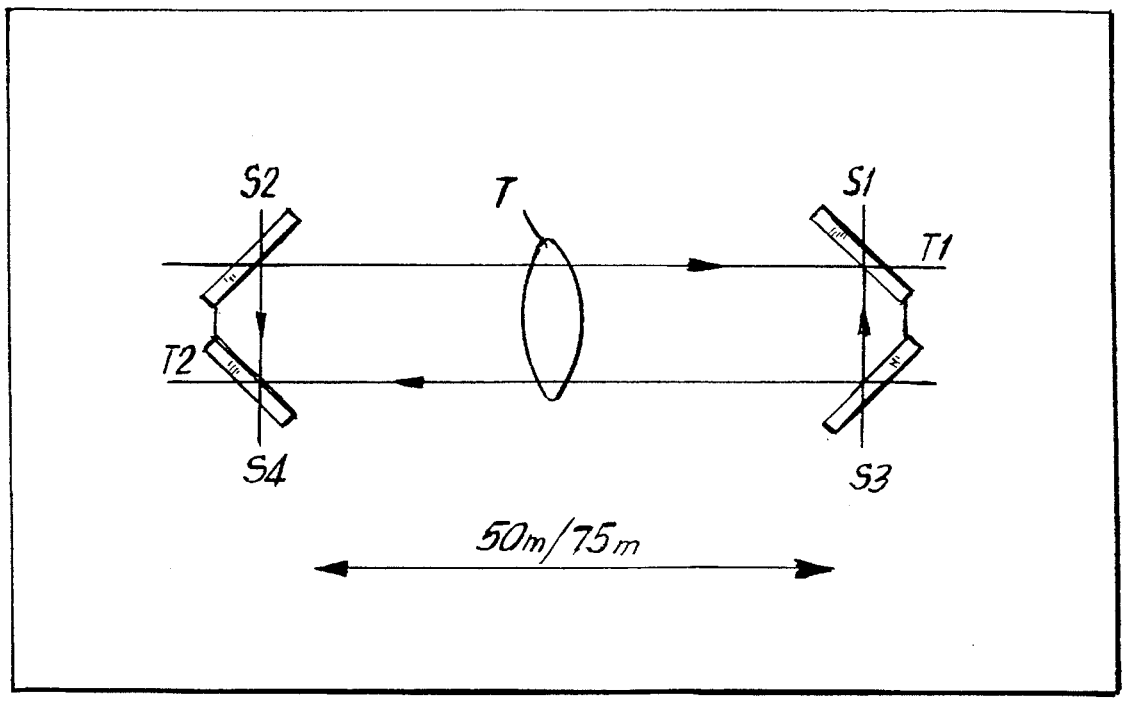
FIG. 4 is a schematic side view of the embodiment shown in FIG. 3 without the transmitters and receivers.

According to a further preferred embodiment as shown in FIGS. 3 and 4, a window 311 having angled sections 37, 39 is provided for both the main beam 31 transmitted by transmitter 35 and the main beam 32 received by receiver 36, respectively.; In this case, each window has its own reference beam path 38, 316 transmitted between transmitter 33 and receiver 34 and between transmitter 314 and receiver 315, respectively. The advantage of this is that a screen can be provided between the two windows in order to prevent optical "crosstalk" between the angled sections. The opposite window 310 includes identical structure to the window 311. It includes a receiver 312 for receiving the transmitted main beam 31 and a transmitter 313 for transmitting the received main beam 32. This window also includes a transmitter 314 and a receiver 315 for the reference beam having a path 316.

Figure 2:
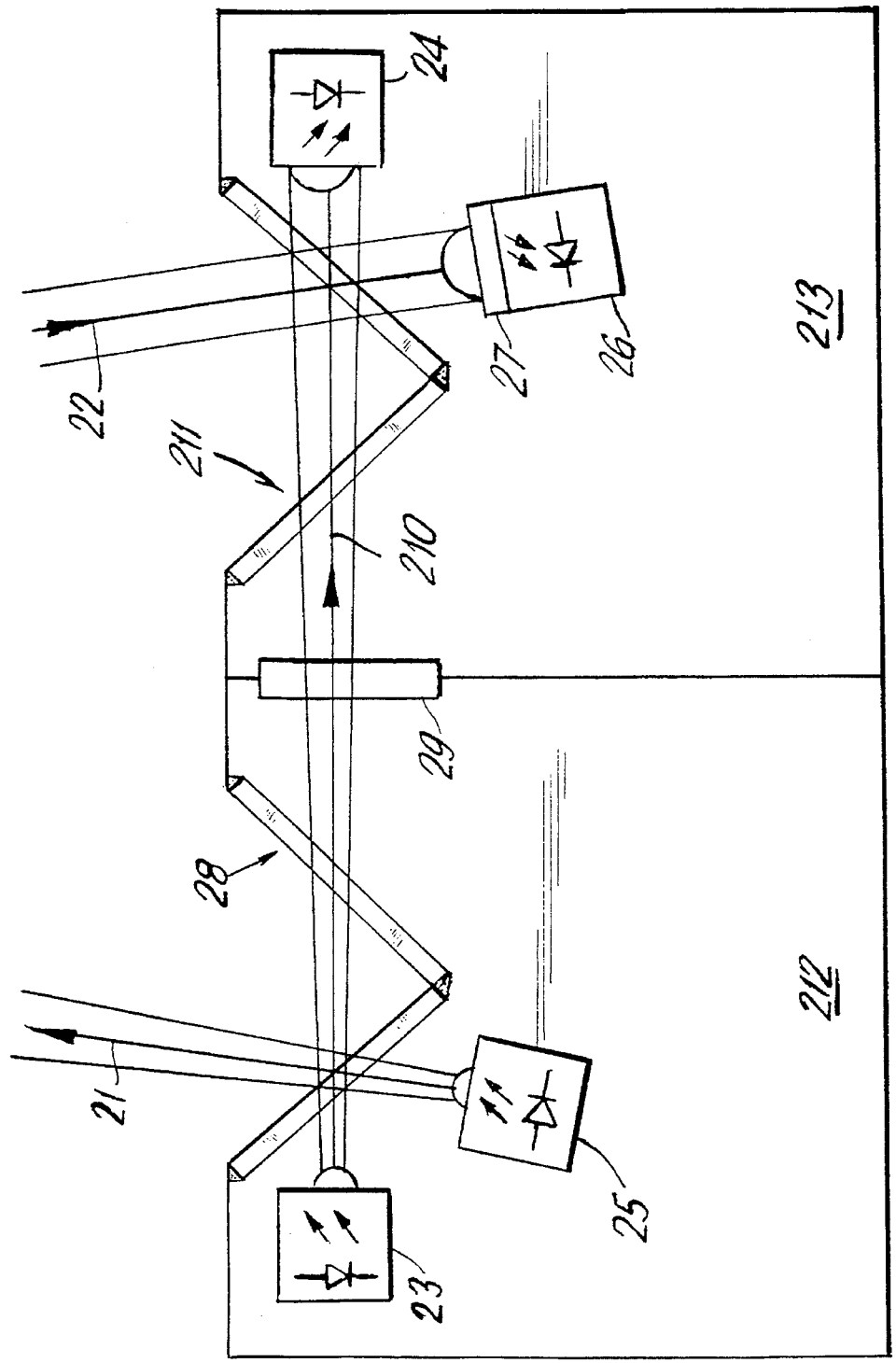
FIG. 2 is a schematic side view of a second embodiment of the present invention.

According to a further preferred embodiment and shown in FIG. 2, a window 212, 213 with angled sections 28, 211 is provided for both the main beam 21 transmitted by transmitter 25 and the main beam 22 received by receiver 26 through optical narrow bank filter 27, respectively, and there is a common reference beam path 210 for both windows 212, 213, and the two windows 212, 213 jointly require only one transmitter 23 and one receiver 24. In addition, a filter 29 is provided between the two windows 212, 213; the filter 29, in narrow-band fashion, allows only the wave length of the reference beam 210 to pass through. The main beam 21 passes through one of the angled sections 28 on the transmitter side 212 and through the other angled section 211 on the receiver side 213.

Preferably, the main beam is transmitted in the range of visible light, while the reference beam is a beam in the infrared range.

According to a further preferred embodiment, the angle between the angled sections of the window equals 90 degrees. According to a special embodiment, the reference beam path is arranged in is such a way that the entire active area of the angled regions is illuminated to determine the contamination of the entire active area integrally.

The invention is explained in greater detail in reference to the examples shown in FIGS. 2 and 3.

FIG. 2 shows:
21) Illuminating cone of main transmitter
22) Field of view of main receiver
23) Reference transmitter with optical system, wavelength 870 nm, intensity controlled and modulated
24) Reference receiver with optical system, photo diode, signal processing
25) Main transmitter with optical system, wave length 650 nm, intensity controlled and modulated
26) Main receiver with optical system, optical narrow-band filter (27), photo diode and signal processing
27) Optical narrow-band filter 650 nm
28) Transmitter-side device lens, arranged at 90° angle
29) Optical narrow-band filter or daylight filter 870 nm
210) Reference measurement beam
211) Receiver-side device lens, arranged at 90° angle
212) Transmitter-side housing part, fully insulated optically from receiver side. No optical cross-talk; single connection via Filter 29) at wave length$\geq$870 nm
213) receiver-side housing part, fully insulated optically from transmitter side FIG. 3 shows:
31) Illuminating cone of main transmitter
32) Field of view of main receiver
33) Reference transmitter with optical system, intensity controlled and modulated
34) Reference receiver with optical system, photo diode, signal processing
35) Main transmitter with optical system, intensity controlled and modulated
36) Main receiver with optical system, photo diode, signal processing
37) Transmitter-side device lens, arranged at 45° angle to main beam direction
38) Reference measurement beam
39) Receiver-side device tens, arranged at 45° angle to main beam direction
310) In the typical arrangement, opposite device part having identical structure Typical distance between the two device parts 50 m or 75 m For the diagram in FIG. 4, the following apply:
T=atmospheric transmission (sought-after quantity)
T1=transmission measurement in 1st measurement segment (containing S1 and S2)
T2=transmission measurement in 2nd measurement segment (containing S3 and S4)
S1=lens contamination value from lens 1
S2=lens contamination value from lens 2
S3=lens contamination value from lens 3
S4=lens contamination value from lens 4
V1=S2*S4=Contamination measurement 1
V2=S1*S3=Contamination measurement 2

With the four values T1, T2, V1 and V2, it is now possible to calculate the lens contamination. What remains is the [voltage] corresponding to the actual transmission T.

The foregoing statement is proved by the following mathematical relationships: from $$T1=T*S1*S2 \text{ and } T2=T*S3*S4$$

it follows that $$T = \sqrt{\frac{T1*T2}{S1*S2*S3*S4}} = \sqrt{\frac{T1*T2}{V1*V2}}$$

In each case, standardized [voltage values] of the appropriate receiver are used as the transmission measurement values or the lens contamination values. Calibration is carried out under visual conditions as close to ideal as possible. The device according to the invention permits the atmospheric transmission to be read directly, regardless of the lens contamination.

I claim:

1. An optical range measurement device comprising:
   at least one window including a first section and a second section positioned in angled relationship to said first section;
   a first transmitter movable between a first position for producing a first main beam having a path extending through said first section into an outer atmosphere and a second position producing a first reference beam for illuminating said first and second sections; and
   a first receiver movable between a first position for receiving said first main beam back scattered by the outer atmosphere and a second position for receiving said first reference beam.

2. The device of claim 1, wherein said first reference beam is produced by said first transmitter to illuminate an entire active area of said at least one window for determining lens contamination.

3. An optical range measurement device, comprising:
   at least one window including a first section and a second section positioned in angled relationship to said first section;
   a first transmitter for producing a first main beam having a path extending through said first section into an outer atmosphere;
   a first receiver for receiving said first main beam back scattered by the outer atmosphere;
   a second transmitter for producing a first reference beam for illuminating said first and second sections; and
   a second receiver positioned for receiving said first reference beam.

4. The device of claim 3, wherein the at least one window includes a first window, and further comprising a second window each including a third section and a fourth section positioned in angled relationship with said third section; and
   a wall positioned between said at least one window and said second window including a filter; said first transmitter positioned for transmitting said first main beam through said first section, said first receiver positioned for receiving said first main beam back scattered by the outer atmosphere through said fourth section, said second transmitter positioned for transmitting said first reference beam for illuminating said first and second sections of said first window, said filter and said third and fourth sections of said second window for receipt by said second receiver.

* * * * *